United States Patent [19]

Ichikawa et al.

[11] Patent Number: 4,789,238

[45] Date of Patent: Dec. 6, 1988

[54] METHOD OF INSPECTING MAGNETIC DISK SURFACE

[75] Inventors: Fusao Ichikawa; Kiyoharu Michimoto, both of Kanagawa, Japan

[73] Assignee: Fuji Photo Film Co., Ltd., Kanagawa, Japan

[21] Appl. No.: 45,993

[22] Filed: May 4, 1987

[30] Foreign Application Priority Data

May 2, 1986 [JP] Japan .............................. 61-102899

[51] Int. Cl.$^4$ ............................................ G01N 21/89
[52] U.S. Cl. ................................. 356/237; 250/563; 250/572; 356/431
[58] Field of Search ............... 356/237, 239, 430, 431; 250/562, 563, 572

[56] References Cited

U.S. PATENT DOCUMENTS

| | | | |
|---|---|---|---|
| 3,274,390 | 9/1966 | Umbel | 250/562 |
| 3,646,353 | 2/1972 | Bhullar et al. | 356/431 X |
| 4,652,124 | 3/1987 | Bowen et al. | 356/237 |

FOREIGN PATENT DOCUMENTS

| | | | |
|---|---|---|---|
| 143205 | 12/1978 | Japan | 356/430 |
| 143193 | 11/1979 | Japan | 356/237 |
| 80009 | 4/1986 | Japan | 356/237 |

*Primary Examiner*—Davis L. Willis
*Assistant Examiner*—Matthew W. Koren
*Attorney, Agent, or Firm*—Sughrue, Mion, Zinn, Macpeak & Seas

[57] ABSTRACT

In a method of inspecting a magnetic disk surface, a magnetic disk web is exposed to a light beam, information on the condition of reflection of the light beam by the magnetic disk web or passing of the light beam through the magnetic disk web is detected, and the condition of surface defects of a magnetic disk is judged based on results obtained by the detected information. The judgement is carried out based on the results at a portion of the magnetic disk web outside of a non-use region of the magnetic disk.

5 Claims, 5 Drawing Sheets

F I G. 5
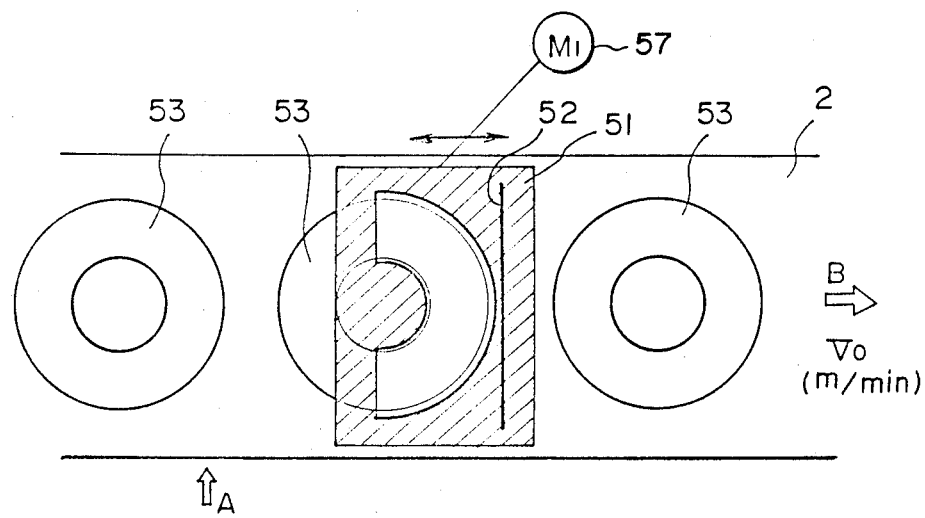
F I G. 6
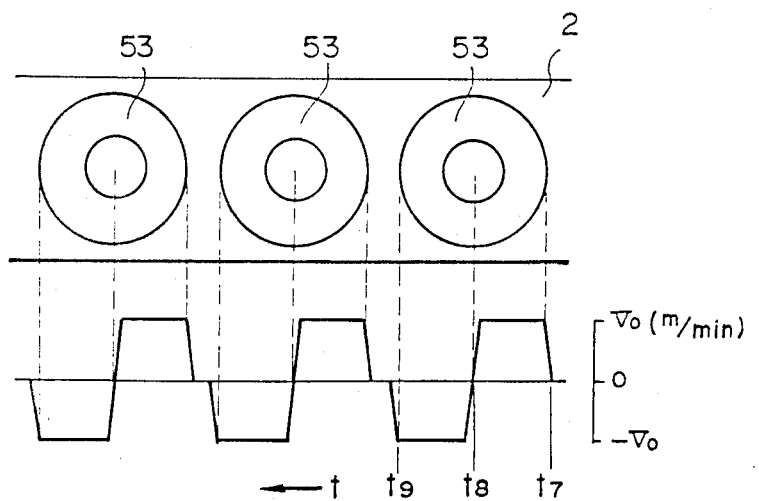

METHOD OF INSPECTING MAGNETIC DISK SURFACE

BACKGROUND OF THE INVENTION

1. Field of the Invention

This invention relates to a method of inspecting defects on a coating film surface of a magnetic disk used as a recording medium for computers or the like. This invention particularly relates to a method of inspecting a magnetic disk surface before magnetic disks are made from a magnetic disk web.

2. Description of the Prior Art

In the course of making magnetic recording media, there has heretofore been used a method wherein a surface of a magnetic recording medium web is exposed to a light beam emitted by a light beam emission means such as a laser, receiving light reflected by the surface of the web by use of a light receiving means provided with a photomultiplier, a solar battery or the like, and detecting changes in the light amount of the reflected light, thereby to inspect defects on the web surface continuously in the web movement direction.

With the conventional technique, no problem arises in the case where a magnetic recording medium of continuous length is to be formed in the web movement direction as in the case of magnetic tapes. However, in the case where diskshaped magnetic recording media are to be made from the magnetic recording medium web as in the case of magnetic disks, some portions of the web are not utilized to form the magnetic disk products, and inspection is carried out also for such portions. Therefore, in the case where no surface defect is present at a portion utilized for forming the magnetic disk product and surface defects are present at a portion which is outside of the portion utilized for forming the magnetic disk product and which is not to be utilized for forming the magnetic disk product, it is not always possible to discriminate the portion having surface defects from the portion having no surface defect. Accordingly, the portion having surface defects plus predetermined lengths on both sides of the defective portion must be rejected for ensuring the quality of the magnetic disk product, and the product yield becomes low.

SUMMARY OF THE INVENTION

The primary object of the present invention is to provide a method of inspecting a magnetic disk surface, which is free from the problem that a non-defective portion of a magnetic disk web is judged to be defective because of surface defects present at a portion not utilized for the formation of a magnetic disk.

Another object of the present invention is to provide a method of inspecting a magnetic disk surface, which improves the yield of magnetic disk products.

The present invention provides a method of inspecting a magnetic disk surface by exposing a magnetic disk web to a light beam, detecting information on the condition of reflection of the light beam by the magnetic disk web or passing of the light beam through the magnetic disk web, and judging the condition of surface defects of a magnetic disk based on results obtained by the detected information, wherein the improvement comprises the step of carrying out said judgment based on said results at a portion of said magnetic disk web outside of a non-use region of the magnetic disk.

With the method of inspecting a magnetic disk surface in accordance with the present invention, judgment of the condition of surface defects on the magnetic disk is carried out based on the results obtained by the information detected at the portion of the magnetic disk web outside of the non-use region of the magnetic disk. Specifically, surface defects at the portion not used as a magnetic disk are not subjected to the judgment, and therefore it is possible to eliminate the problem that the non-defective web portion around surface defects is processed as a defective portion when the surface defects are present at the web portion not utilized as a magnetic disk. Accordingly, it becomes possible to improve the yield of the magnetic disk products.

The term "magnetic disk" as used herein embraces the case where the magnetic recording medium is exactly circular in shape and the case where it has a polygonal shape.

By the term "magnetic disk web" is meant an original magnetic disk sheet from which magnetic disks are to be formed by cutting or punching out. Normally, a strip-like film wound in a roll form is used as the magnetic disk web.

The light beam is emitted by a point light source such as a laser beam source, or a linear light source such as an LED array. In general, the light beam is scanned on the magnetic disk web in a main scanning direction and in a sub-scanning direction in the case where the light beam is emitted by the point light source, or in the sub-scanning direction in the case where the light beam is emitted by the linear light source.

By the term "information on the condition of reflection of a light beam by a magnetic disk web or passing of the light beam through the magnetic disk web" is meant at least one of various information items on the surface of the magnetic disk web, which the light beam reflected by the web or the light beam passing through the web carries. For example, the information on the condition of reflection or passing means the amount of the reflected light or the amount of the passing light.

The results obtained by the detected information may be the direct results such as the number and the sizes of the surface defects, or the indirect results obtained by judging the surface condition based on the direct results.

The term "non-use region of a magnetic disk" means the region of the magnetic disk web outside of the region used as the recording and reproducing region when the magnetic disk is made from the magnetic disk web. The non-use region of the magnetic disk embraces a region outside of the magnetic disk and a region inside of the magnetic disk. Also, "a portion of the magnetic disk web outside of a non-use region of the magnetic disk" may be the inside of the circular portion corresponding to the outer shape of the magnetic disk, or may be only the track region contributing to signal recording and reproduction. Thus the term "a portion of the magnetic disk web outside of a non-use region of the magnetic disk" does not necessarily mean the web portion completely outside of the non-use region of the magnetic disk, and may include a part of the non-use region of the magnetic disk.

Various methods may be used for obtaining the aforesaid results concerning the predetermined region as mentioned above. For example, an optical mask may be applied to the region of the magnetic disk web, which should constitute the non-use region of the magnetic disk, thereby to eliminate the information on surface defects outside of the predetermined region. Or, after the information is continuously detected from the magnetic disk web, signals representing the information may be conducted to a gate which is opened only for the period corresponding to the predetermined region, and the aforesaid results may be obtained only from the information represented by the signals passing through the gate. The aforesaid results concerning the predetermined region may also be obtained by use of a software technique utilizing a microcomputer instead of the gate.

BRIEF DESCRIPTION OF THE DRAWINGS

FIG. 6 is a timing chart showing the movement speed of the optical mask shown in FIG. 5.

DESCRIPTION OF THE PREFERRED EMBODIMENTS

The present invention will hereinbelow be described in further detail with reference to the accompanying drawings.

Figure 1A:
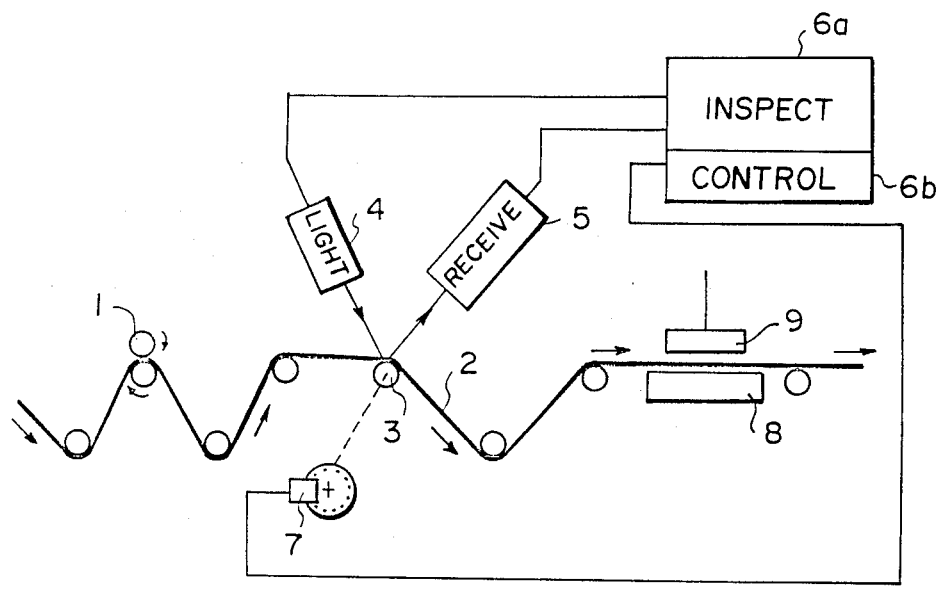
FIGS. 1A and 1B are schematic views showing embodiments of the method of inspecting a magnetic disk surface in accordance with the present invention.

Referring to FIG. 1A, a magnetic disk web 2 is polished by a polishing device 1, and the coating film surface of the magnetic disk web 2 is exposed at an inspection roll 3 to a light beam emitted by a light emitting device 4 constituted by a laser or the like. The light beam reflected by the coating film surface of the magnetic disk web 2 is received by a light receiving device 5 provided with a photomultiplier, and signals based on changes in the light amount of the reflected light beam are waveform processed by an inspecting device 6a, thereby to inspect whether defects are present or not on the coating film surface. In this embodiment, in the course of the inspection, the length of the magnetic disk web 2 passing over the inspection roll 3 is measured by detecting the extent of rotation of the inspection roll 3 by use of an encoder 7, and pulse signals generated by the encoder 7 are fed to an inspection range control device 6b. In this manner, the inspection range is changed sequentially so that, as indicated by a hatched area (inspection range) 11 in FIG. 2, only the range approximately corresponding to the recording and reproducing region of the magnetic disk can be inspected. Also, a punching device constituted by members 8 and 9 is synchronized with the inspecting operation for punching out only the range approximately corresponding to the recording and reproduction region of the magnetic disk as the final product. Therefore, inspection for defects outside of said range is not performed, and there is no risk of the magnetic disk as the final product being judged as a defective product because of defects present on the web outside of the magnetic disk as with the conventional technique. Accordingly, it is possible to markedly improve the yield of the magnetic disks or the like in the production process.

Figure 2:
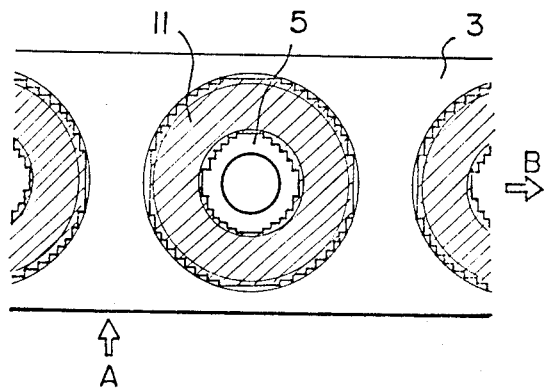
FIG. 2 is a schematic view showing an example of the inspection range in the embodiments of FIGS. 1A and 1B, FIGS. 3 and 4 are a circuit diagram and a timing chart showing the method of controlling the inspection range in the embodiments of FIGS. 1A and 1B, FIGS. 5 and 7 are schematic views showing examples of the inspection ranges in further embodiments of the method of inspecting a magnetic disk surface in accordance with the present invention.
Figure 3:
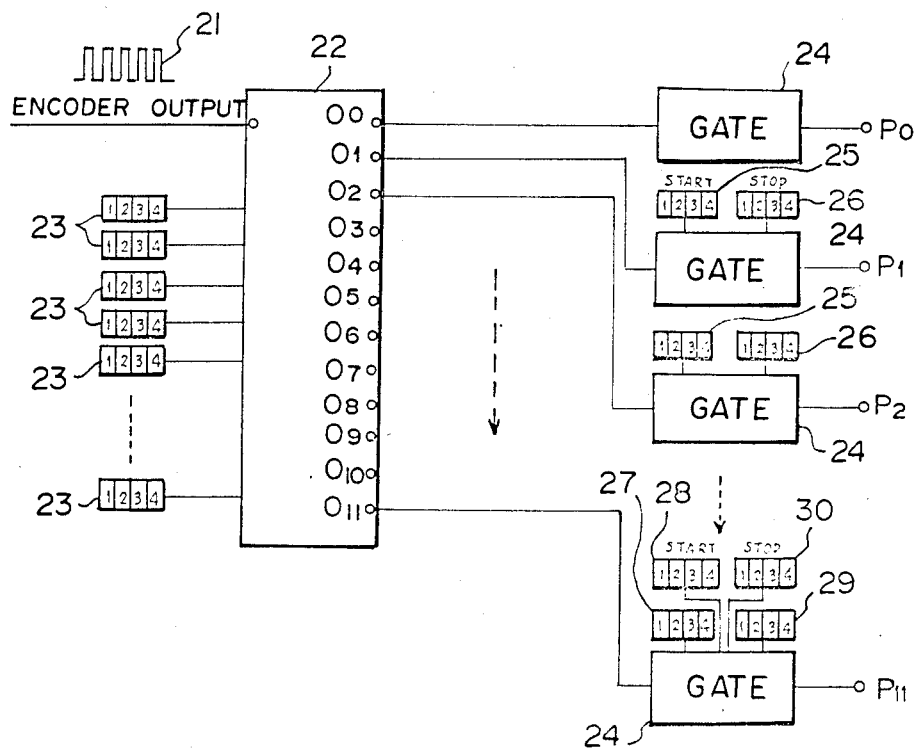
Figure 4:
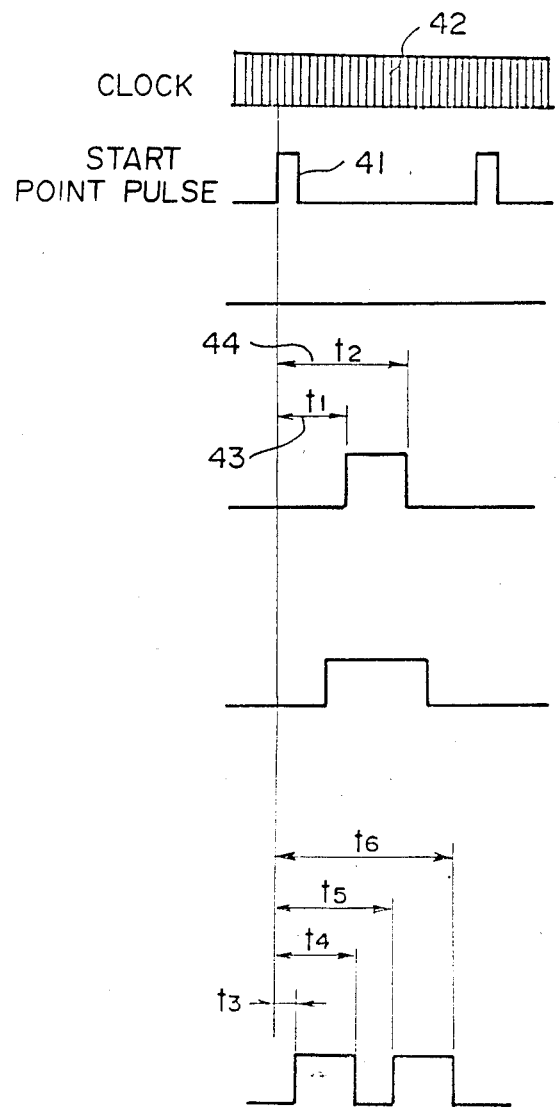

The method of controlling the inspection range will hereinbelow be described in further detail with reference to FIGS. 2, 3 and 4. In FIG. 2, the light beam such as a laser beam emitted by the light emitting device 4 as shown in FIG. 1A is scanned by a polygon mirror or a galvanometer mirror in the width direction of the magnetic disk web as indicated by the arrow A. In this case, the inspection range in the width direction of the magnetic disk web is sequentially changed in the web movement direction as indicated by the arrow B so that the range approximately corresponding to the recording and reproducing region of the magnetic disk can be inspected as indicated by the inspection range 11. An example of the method of controlling the inspection range will now be described with reference to FIG. 3. Pulses of a pulse input signal 21 generated by the encoder 7 are counted by a multi-stage up-and-down counter circuit 22. The output of each stage is shifted sequentially from a stage 0 to a stage 1, then to a stage 2, and so on in accordance with the value set at a preset value setting digital switch 23 of each stage. When a step 11 is counted up, a subtraction operation is started to shift down from the stage 11 to a stage 10, then to a stage 9, and so on down to the stage 0. These operations are repeated. Thus gate-wise circuits 24, 24, ... for adjusting the inspection range are sequentially changed over, and the inspection range is changed over as shown by the timing chart of FIG. 4. In this manner, the inspection range 11 as indicated by the hatching in FIG. 2 is obtained. Based on values set at an inspection gate start setting digital switch 25 and an inspection gate stop setting digital switch 26, the gate-wise circuit 24 for adjusting the inspection range begins counting of clock pulses 42 from the leading edge of a scanning start point pulse 41. The inspection gate is opened with an inspection gate start timing t1 43 as shown in FIG. 4, and closed with an inspection gate stop timing t2 44. At the center portion of the magnetic disk, it is necessary to open the gate twice. For this purpose, two inspection gate start digital switches 27, 28 and two inspection gate stop digital switches 29, 30 are connected to the gate-wise circuit 24 at the stage 11 as shown in FIG. 3, and the inspection gate is opened twice as shown in FIG. 4.

In the aforesaid embodiment, the multi-stage up-and-down counter circuit 22 is of eleven stages, and eleven stages of the gate-wise circuits 24, 24, ... are provided. However, the number of the stages may be increased or decreased. When the number of the stages is increased, it becomes possible to make the inspection range closer to a disk shape.

Also, in the aforesaid embodiment, many digital switches, i.e. the preset value setting digital switches 23, 23, ..., the inspection gate start digital switches 25, 25, 27 and 28, and the inspection gate stop digital switches 26, 26, ..., 29 and 30, are used. However, instead of using many digital switches, the settings may be effected by, for example, software by use of a computer.

Further, instead of using the start point of light beam scanning for creating the start point pulse 41, the edge portion of the magnetic disk web 2 may be detected and used for creating the start point pulse 41. In this case, it becomes possible to eliminate adverse effects of zigzag movement of the magnetic disk web 2.

In the aforesaid embodiment, the multi-stage up-and-down counter circuit 22 is used for the purpose of changing over the inspection range. However, the present invention is not limited to the use of the multi-stage up-and-down counter circuit 22, and any method may be used insofar as the pulses of the pulse input signal 21 generated by the encoder 7 are counted and the output of the circuit is sequentially changed over in accordance with a preset value. For example, a combination of a multi-stage preset counter with a logic circuit may be used for this purpose.

Also, instead of using the encoder 7 for measuring the length of the magnetic disk web 2 passing over the inspection roll 3, the length of the magnetic disk web 2 may be measured by counting the movement time of the magnetic disk web 2 by use of a timer circuit.

Figure 1B:
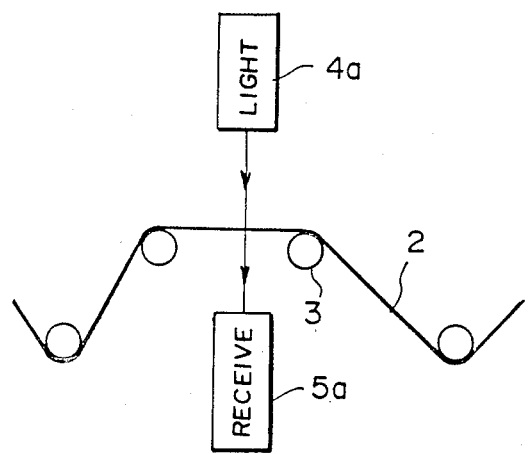

In the aforesaid embodiment, defects are inspected based on changes in the amount of light reflected by the surface of the magnetic disk web 2. However, as shown in FIG. 1B, defects may be inspected based on changes in the amount of light passing through the magnetic disk web 2. In the embodiment of FIG. 1B, the magnetic disk web 2 is exposed to a light beam such as a laser beam emitted by a light emitting device 4a, and the light beam passing through the magnetic disk web 2 is received by a light receiving device 5a provided with a photomultiplier, and signals based on changes in the light amount of the light beam passing through the magnetic disk web 2 are waveform processed by the inspecting device 6a as shown in FIG. 1A, thereby to inspect whether defects are present or not on the surface of the magnetic disk web 2. Defects may also be inspected for by combining the detection of the amount of the light beam reflected by the magnetic disk web 2 with the detection of the amount of the light beam passing through the magnetic disk web 2.

Further embodiments of the method of inspecting a magnetic disk surface in accordance with the present invention will hereinbelow be described in detail. FIG. 5 schematically shows the method of changing the inspection range by application of an optical mask, and FIG. 6 is a timing chart showing the movement speed of the optical mask as shown in FIG. 5. In FIG. 5, an optical mask 51 is disposed between the light emitting device 4 as shown in FIG. 1A and the magnetic disk web 2. The optical mask 51 is alternately moved forwardly and backwardly in the web movement direction, thereby to obtain the same effect as movement of light 52 emitted by a linear light source or formed by scanning a light beam in the width direction of the magnetic disk web 2. As a result, it is possible to expose only the range approximately corresponding to the recording and reproducing region of the magnetic disk to the light 52. Light reflected by the magnetic disk web 2 is detected, and defects on the magnetic disk web 2 are inspected for. Accordingly, even though defects are present on the magnetic disk web 2 outside of the magnetic disk formed as the final product, there is no risk of a predetermined web range around defects being processed as a defective portion. Thus it becomes possible to markedly improve the yield of the magnetic disks in the production process.

The operation of the optical mask 51 will hereinbelow be described with reference to FIGS. 5 and 6. The optical mask 51 is moved by a drive motor M1 57 in synchronization with the movement of the magnetic disk web 2. The relationship between the position of the optical mask 51 and the position of the light 52 as shown in FIG. 5 is set as the initial conditions. A head timing t7 of the recording and reproducing regions 53, 53, 53 of the magnetic disks on the magnetic disk web 2 is used as a trigger as shown in FIG. 6, and the optical mask 51 is moved in the movement direction of the magnetic disk web 2 as indicated by the arrow B at the same time speed Vo (m/min.) as the magnetic disk web 2. In this manner, only a semicircular portion of the recording and reproduction region 53 of the magnetic disk is exposed to the light 52, and the surface of the semicircular portion is inspected. With a timing t8 at the center of the magnetic disk, the optical mask 51 is moved reversely to the movement direction of the magnetic disk web 2 for exposing the remaining semicircular portion of the recording and reproducing region 53 of the magnetic disk to the light 52 and carrying out the surface inspection of said remaining semicircular portion. The optical mask 51 is stopped at an end timing t9, and the same operation is repeated from the head of the recording and reproducing region 53 of the next magnetic disk. In this manner, only the recording and reproducing regions 53, 53, 53 of the magnetic disks are inspected over the overall length of the magnetic disk web 2.

Figure 7:
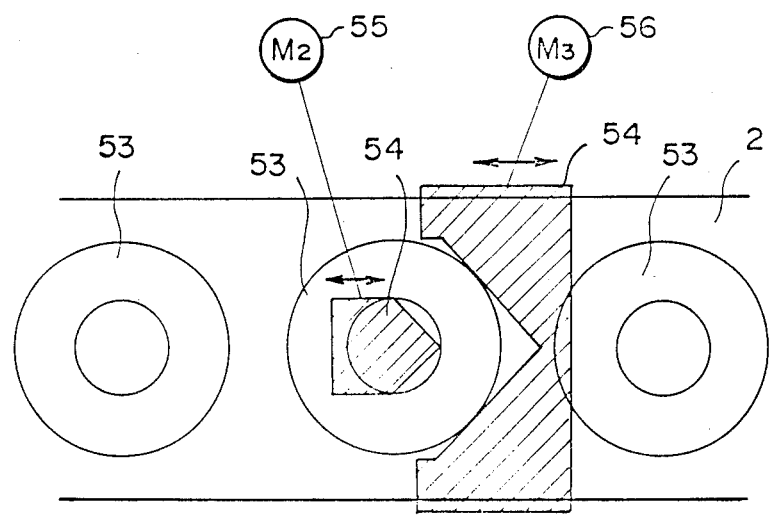

Though the optical mask 51 having a shape as shown in FIG. 5 is used in the aforesaid embodiment, the shape of the optical mask is not limited to the shape as shown in FIG. 5. For example, optical masks 54, 54 as shown in FIG. 7 may be used. Also, the width of exposure to light may be controlled by moving the optical masks 54, 54 by use of, for example, two drive motors, i.e. a drive motor M2 55 and a drive motor M3 56.

In the embodiments of FIGS. 5 and 7, the optical mask 51 is moved by the drive motor, or the optical masks 54, 54 are moved by the drive motors. However, the present invention is not limited to such a movement method. For example, it is also possible to move the optical mask 51 or the optical masks 54, 54 in exact synchronization with the web movement system by, for example, moving a mechanical cam by use of a power system for web movement.

We claim:

1. A method of inspecting a magnetic disk surface by exposing a magnetic disk web to a light beam, detecting said light beam following exposure to said magnetic disk web, and judging the condition of surface defects of a magnetic disk based on results obtained by the detected information, wherein the improvement comprises the step of carrying out said judgment based on said results at a portion of said magnetic disk web outside of a non-use region of the magnetic disk.

2. A method as defined in claim 1 wherein said results at the portion of said magnetic disk web outside of the non-use region of the magnetic disk are obtained by feeding a signal representing said information to a gate opened in response to a period of detection of said portion of said magnetic disk web outside of the non-use region of the magnetic disk, and obtaining said results from said information which said signal passing through said gate represents.

3. A method as defined in claim 1 wherein said results at the portion of said magnetic disk web outside of the non-use region of the magnetic disk are obtained by masking at least a part of said non-use region of the magnetic disk on said magnetic disk web, and obtaining said results from said information detected in the condition of said masking.

4. A method as defined in claim 1 wherein the step of detecting said light beam comprises detecting said light beam as it is reflected from said magnetic disk surface to obtain information on the condition of reflection of said light beam.

5. A method as defined in claim 1 wherein the step of detecting said light beam after it passes through said magnetic disk web.

* * * * *